United States Patent [19]

Bonnefous

[11] Patent Number: 5,579,771
[45] Date of Patent: Dec. 3, 1996

[54] METHOD OF AND APPARATUS FOR THE DETECTION AND CHARACTERIZATION OF A SEGMENT OF AN ARTERY BY ULTRASONIC ECHOGRAPHY

[75] Inventor: Odile Bonnefous, Nogent, France

[73] Assignee: U.S. Philips Corporation, New York, N.Y.

[21] Appl. No.: 413,298

[22] Filed: Mar. 27, 1995

[30] Foreign Application Priority Data

Mar. 25, 1994 [FR] France .................................. 94 03557

[51] Int. Cl.⁶ .................................................. A61B 8/00
[52] U.S. Cl. .................................................. 128/661.04
[58] Field of Search .................... 128/660.01/661.04, 128/661.08–661.1; 73/861.25

[56] References Cited

U.S. PATENT DOCUMENTS 4,803,990 2/1989 Bonnefous et al. ............... 128/661.08
5,107,840 4/1992 Bonnefous ........................ 128/661.08
5,411,028 5/1995 Bonnefous ........................ 128/661.08

FOREIGN PATENT DOCUMENTS 0225667 11/1986 European Pat. Off. .
2563991 4/1985 France .

*Primary Examiner*—Francis Jaworski
*Attorney, Agent, or Firm*—Edward Blocker

[57] ABSTRACT

An echograph of the type involving signal processing in the time domain with correlation-interpolation of the echographic signals is adapted to measure radial displacement velocities of the walls of an artery. A frame is scanned with a period T of a few ms at a rate of one excitation per line, and the correlations-interpolations are performed between collinear excitation lines shifted by the period T (52), enabling velocity values V(x,z,t) to be obtained for storage in a first memory (55) and amplitude values A(x,z,t) for storage in a second memory (57). These values are subsequently processed (60) in order to deduce dilatation and compression curves therefrom.

19 Claims, 4 Drawing Sheets

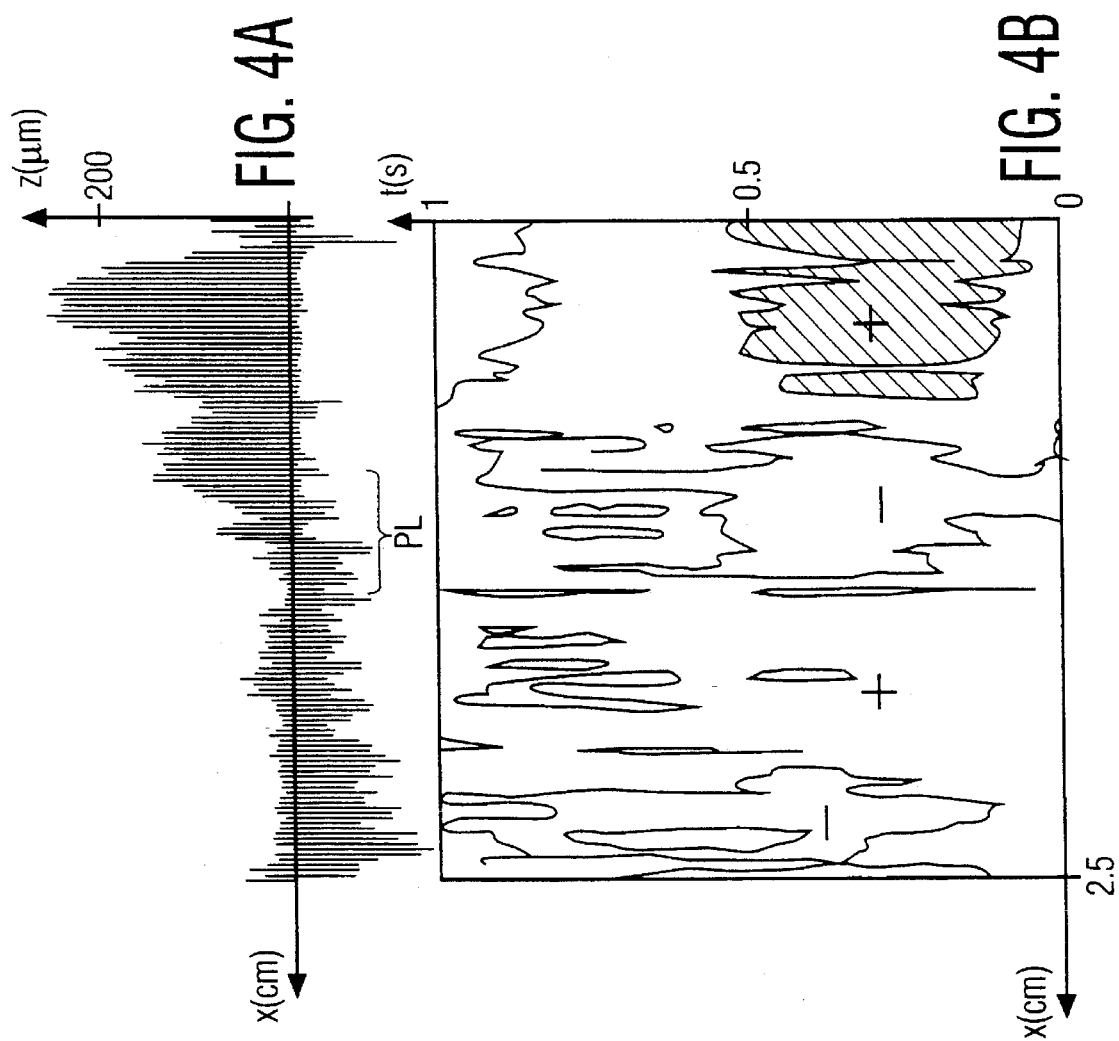
FIG. 4A
FIG. 4B
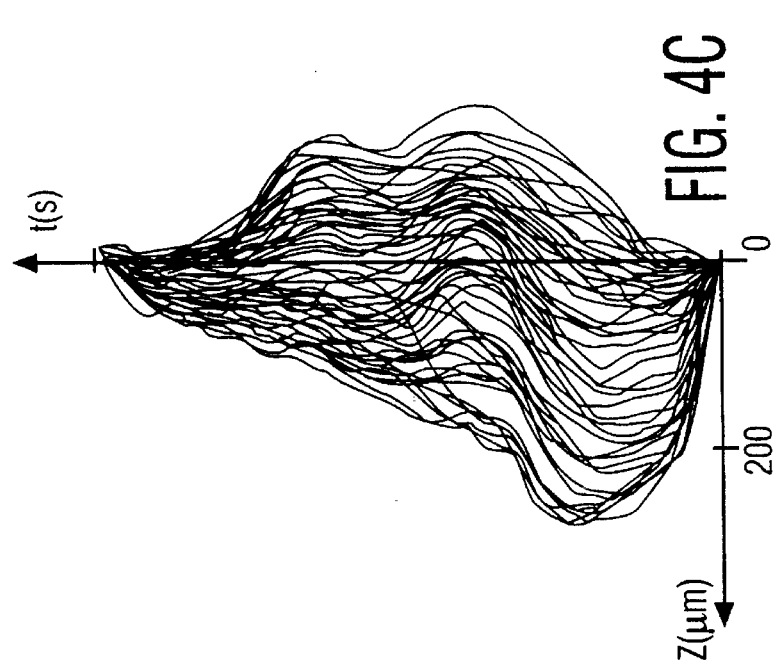
FIG. 4C

METHOD OF AND APPARATUS FOR THE DETECTION AND CHARACTERIZATION OF A SEGMENT OF AN ARTERY BY ULTRASONIC ECHOGRAPHY

BACKGROUND OF THE INVENTION

1. Field of the Invention

The invention relates to a method of detecting and characterizing a segment of an artery by ultrasonic echography, using an array of ultrasonic transducers which produce a sectional plane or frame which is formed by L successive parallel excitation lines in a direction $\vec{z}$ which extends perpendicularly to the axis $\vec{x}$ of the artery, which array is associated with a transmitting circuit and a receiving circuit, said echography method being of the type involving signal processing in the time domain with correlation of the echographic signals relating to said lines and interpolation of the correlated signals in order to determine radial velocities v for points of said sectional plane which are limited to the traversing of the walls of the artery and its immediate vicinity.

In order to carry out the above method, the invention also relates to an apparatus for the detection and characterization of a segment of an artery, comprising an ultrasonic echograph and a work station, the echograph consisting of a probe provided with an array of ultrasonic transducers conceived to emit a frame of L successive lines during a period T in a direction $\vec{z}$ which extends perpendicularly to the axis $\vec{x}$ of the artery, a transmitting circuit and a receiving circuit, which echograph is of the type involving signal processing in the time domain for which purpose it comprises correlation means and interpolation means for the echographic signals.

2. Description of the Related Art

Methods and apparatus of this kind, suitable for use in the medical field, are particularly important for the characterization of a stenosis which may already have been detected either by angiography or by means of the ultrasonic probe itself.

An echograph is an apparatus for the examination of media, utilizing the ultrasonic radiation as an information source. An apparatus of this kind utilizes a step for the transmission of ultrasonic signals to the medium scanned by periodic excitations, as well as a step for the reception and processing of the echos returned by the obstacles encountered in the medium scanned. The two steps are executed by means of the same ultrasonic probe which is in contact with the medium. This probe is a construction which, generally speaking, is composed of a network of ultrasonic transducers which are assembled in the form of a linear array. It emits at a central frequency fo of the order of magnitude of a few MHz.

During the transmission step, the medium is selectively scanned along a line. In the receiving mode, the image of this scanned line is formed, taking into account the time of flight in the medium and the amplitude of the echos from the various obstacles encountered along the line. The image of a sectional plane is formed by the scanning of this line. In order to obtain a high image resolution, it is desirable to scan the medium very selectively by way of focused ultrasonic excitation and, in the receiving mode, to select the echos stemming from the same line by utilizing a focusing aperture.

A contemporary focusing technique consists of the use of a linear network of transducers and of defining, in the transmission mode, an incident beam which is focused by means of a delay rule imposed on the transducer excitation pulses. In the receiving mode, focusing is then achieved in a similar manner by suitably delaying the signals received by each of the transducers of the network, prior to their summing and later processing. This processing of the signals in the receiving mode, resulting in a signal of high amplitude for the echos stemming from the focal point (which point is situated on the line scanned) and in weak signals for all other echos is customarily referred to as a beam-forming method.

In order to achieve suitable focusing along an entire line, contemporary echographs utilize a focusing rule in the receiving mode which, generally speaking, is not continuous but subdivided into zones of the order of magnitude of a centimeter (cm) in the direction $\vec{z}$ of excitation. In the transmission mode, several beams which are focused to different depths are successively transmitted in the same direction. Consequently, it is to be noted hereinafter that when the part to be analyzed within an organism is small, for example of the order of magnitude of 2 by 3 cm, it may be that a single focusing zone suffices so that only one transmission is required, thus enabling the analysis frame frequency to be increased.

The use of linear networks of transducer elements not only enables focusing, but also the execution of the scanning necessary for the formation of a two-dimensional image on the screen of a conventional echographic monitor (2 D imaging). For the examination of, for example a segment of an artery of an order of magnitude of 3 cm, a frame of 128 lines which are spaced 0.25 mm apart may be used.

For non-invasive in vivo examination of an artery it is found that the detection and the evaluation of stenoses, both in respect of their origin and their seriousness, are an important goal for ultrasonic medical applications. Measurements utilizing the Doppler technique for the ultrasonic echos constitute the prime means of examination utilized by radiologists for this purpose. However, it .appears that the medical diagnosis results from criteria which are not very objective, such as the percentage of the reduction of the useful lumen area of the artery, or of the pressure gradient estimated on the basis of the Doppler measurement of the speed of the blood in the stenosis. Even though these methods are clinically renowned, it seems that they are only makeshift means which are not very accurate.

After detection of a stenosis, the physician must decide whether surgical intervention is necessary or a simple angioplasty (local dilatation) suffices. The latter is performed if the stenosis reduces the useful lumen area of the artery by not more than 70%, whereas the first solution is chosen when the vessel is almost occluded. In parallel with the morphologic detections by ultrasound or angiography, the velocity of the blood is the preferred parameter measured either by Doppler systems or by CVI (Colour Velocity Imaging) systems as described notably in the annual review L.E.P (Laboratoires d'Électronique Philips) 1990, in the article "De l'algorithme au produit", pp. 43, 44, by O. Bonnefous.

The simplified Bernoulli equation $V^2 = \Delta P$ (where V and P are the blood velocity and pressure, respectively) is supposed to provide an indication of the pressure gradient across the stenosis. However, this characterization is not specific enough, probably because the Bernoulli equation used does not correspond to the propagation phenomenon describing the relations between the pressure and the blood flow in the arterial system. Physicians are led to classify the stenoses in two groups, one group being qualified as significantly hemodynamic and the other as non-significantly hemodynamic, because the alteration of the vessel cannot be quantified. Moreover, an apparent contradiction exists between the fact that the blood velocity increases within the stenosis because of and in proportion to the reduction of the useful lumen area, and the fact that this velocity subsequently decreases abruptly when this useful lumen area decreases to the point where it causes a thrombus (artery nearly occluded). Hereinafter a more refined mathematical analysis will be developed, enabling this strange hemodynamic behaviour to be taken into account and forming a new approach to the characterization of stenoses. It will be demonstrated that the means proposed by the invention for the observation and the associated measurements in conformity with the in vivo acquisitions concerning normal and pathological cases are very well compatible with this new approach to the characterization of stenoses.

For the past ten years research has been carried in the field of ultrasonic echography in order to find out whether accurate characterization of the pulsating movement is possible, particularly of a given artery segment, especially to find out whether a part of the artery exhibiting a stricture (constriction, stenosis, atherosclerosis) can thus be characterized. In this respect reference can be made to French Patent Application FR-A-2 563 991 which proposes to search, for two excitation lines traversing a vessel, the boundaries of this vessel and the variation of these boundaries in the course of time, resulting in two dilatation curves which are slightly shifted in time, said shift being representative of the transmission time of the pressure wave, between the two excitation lines, within the vessel. For this manipulation use is made of a Doppler-type ultrasonic scanograph. However, such a principle for the measurement of echos lacks refinement and the means adopted to determine the position of the walls of the vessel are not very exact. On the other hand, it is not possible to construe more than two dilatation curves in the course of the same cardiac cycle; this is a source of irregularities during the rearrangement of the curves representing the analyzed segment of the vessel.

SUMMARY OF THE INVENTION

It is an object of the present invention to characterize a healthy or stenosed arterial segment on the basis of precise information acquired in vivo from this arterial segment along numerous closely spaced excitation lines during a cardiac cycle by utilizing an echographic apparatus based on signal processing in the time domain with signal correlation-interpolation.

It is another object of the invention to determine, for a stenosed arterial segment, a cut-off frequency value fc below which the fundamental cardiac frequency as well as its first harmonics are not transmitted, only the higher frequency harmonics, i.e. of a frequency higher than fc, being transmitted with a given damping.

These objects are achieved, and the drawbacks of the prior art are mitigated, in that the method of the kind set forth in the first paragraph is characterized in that, said frame being scanned with a period T of a few ms at a rate of one excitation per line, said correlation and interpolation are performed between collinear excitation lines shifted by the period T in order to obtain, at least for the duration of one cardiac cycle, in a first memory a first sequence of images in $\vec{x}$ and $\vec{z}$ of velocity values $v(x,z,t)$, in a second memory a second sequence of images in $\vec{x}$ and $\vec{z}$ of amplitude values $A(x,z,t)$, and in that said velocity and amplitude values are subsequently used in the work station in order to deduce therefrom, by temporal integration of the velocity values, the arterial dilatation curve along each of said L frame lines during at least the period Tc of a cardiac cycle.

A preferred version of the method is characterized in that the following operations are performed by the workstation:
a) the thresholding of the amplitudes in order to identify the two diametrically opposite arterial walls,
b) the spatial averaging according to $\vec{z}$ of the velocities in each wall,
c) the temporal integration of the two velocities thus averaged, with correction of the movements of the assembly in order to deduce therefrom the dilatation values $D(x,t)$ of the walls, and the arterial dilatation curves along each of the L frame lines, said curves being associated with the period Tc of the cardiac cycle,
d) the rephrasing of said dilatation curves as necessitated by the time shifts imposed on the L lines of each frame.

In order to carry out the described method use can be made notably of the apparatus described in EP 0 225 667 which corresponds to commonly owned U.S. Pat. No. 4,803, 990 (incorporated herein by way of reference), which apparatus operates according to the time correlation principle (1 bit) and which offers exact velocity measurements because these measurements are independent of the ultrasonic frequency. The unit for measuring the blood flow velocity in this apparatus notably comprises, inserted in a digital processing channel, a correlation circuit which supplies correlation function values on the basis of two excitation lines which succeed one another in time but which are collinear with a given excitation axis, and a multiplexing-interpolation circuit which supplies, on the basis of said correlation function values, an estimate of the velocity $V(t,z)$ of the media traversed, i.e. instantaneous velocity profiles according to the excitation axis. When this concerns the displacement of blood, a device is required for the suppression of fixed echos, i.e. the very strong echos which are due to the arterial walls whose very low displacement velocities may be considered to be negligible since they are approximately 100 times slower. More generally speaking, when the blood flow is not particularly concerned a fixed-echo suppression device is not necessary, as is the case for carrying out the present invention which concerns notably the radial displacements of the walls of an artery.

However, a constraint which could limit the use of an echograph is what is referred to as aliasing which prevents the estimation of absolute velocities beyond a given limit velocity:

$$Vlim = \frac{C_{us}}{4} \frac{F}{fo} \tag{0}$$

in which $C_{us}$ represents the propagation velocity of the ultrasonic wave and F is the recurrent frequency of the excitation of the transducers. This phenomenon is linked to the indetermination induced by the periodicity of the echographic signal. A detailed description thereof is given in "Doppler Ultrasound and Its Use in Clinical Measurement", P. Atkinson and J. P. Woodcock, Academic Press, 1982.

For example, in the case of a recurrent period 1/F of 100 μs, a central acoustic frequency fo of 5 MHz and a propagation velocity $C_{us}$ of 1500 m/s, a limit velocity of 75 cm/s is obtained; most of the time this is suitable for the measurement of blood velocities. However, noting that the arterial displacements are approximately 100 times slower than those of blood corpuscles, the recurrent period 1/F can be multiplied by a factor 100 to make it equal to approximately 10 ms, all other circumstances remaining the same, i.e. without decreasing the frequency fo which would reduce the precision of the measurement and the resolution.

The basic idea of the invention consists in taking advantage of the fact that this recurrent period of collinear excitations can be increased so as to make it equal to one frame period. Actually a reduced frame is involved, comprising some hundred lines with a small range, because of a single focusing with line-wise emission as already stated, so a few square centimeters, but this suffices for the analysis of a stenosis. It is thus possible to conceive a new imaging mode which very accurately visualizes the motions of the walls of an arterial segment, the instantaneous information thus obtained also being digitized, resulting in a very flexible use, notably for different types of representation in $\vec{x}, \vec{z}, t$ by means of a work station, by those skilled in the art.

In these circumstances an apparatus as described in the second paragraph for carrying out the methods described above is characterized in that said transmission circuit comprises first means for performing a single excitation per frame line, that said receiving circuit comprises second means for performing said cross-correlations and interpolations between collinear excitation lines shifted by the period T, that it also comprises a first memory for a sequence of images $\vec{x}$ and $\vec{z}$ of velocity values v(x, z, t) and a second memory for sequences of images in $\vec{x}$ and $\vec{z}$ of amplitude values A(x,z,t) for the duration of at least one cardiac cycle, and that said work station comprises means for utilizing the contents of said first and second memory and for deducing therefrom elongation values as well as dilatation curves for the arterial segment analyzed.

An attractive embodiment of the apparatus is characterized in that said work station comprises:
a) thresholding means for thresholding said amplitudes A(x,z,t) according to $\vec{z}$ in order to identify the two arterial walls,
b) averaging means for forming a spatial mean value according to $\vec{z}$ of the velocity information v(x,z,t) in each wall,
c) integration means for performing the integration in time of the two velocities thus averaged, including correction of the movements of the assembly, in order to deduce therefrom the dilatation values D(x,t) of the walls, and the arterial dilatation curves along each of the L frame lines, said curves being associated with the period of the cardiac cycle,
d) dephasing means for performing the rephrasing of said dilatation curves as necessitated by the time shifts imposed on the L lines of each frame.

In the case of stenoses, the arterial wall is severely damaged, which strongly disturbs its operation. Thanks to its own elasticity, a healthy artery behaves as a propagation line. When plaque or stenoses appear in various areas, the elasticity changes and as a result the propagation phenomenon is disrupted. An object of the invention is to evaluate the repercussions of the diseased arterial wall on its operation as a propagation line by analyzing the arterial dilatation during the cardiac cycle. Because the living material constituting the artery is elastic, a first-order linear relationship exists between the variations of the diameter of the artery and those of the pressure. Because of this consideration, the external measurement of the diameter is to be preferred over the (invasive) measurement of the arterial pressure.

The blood flow rate and the pressure (or rather the arterial diameter) are conjugated parameters which propagate with the same propagation velocity. The two equations describing the relations between flow rate and pressure in an elastic tube (without friction) are:

$$S \frac{dV}{dx} + \frac{dS}{dt} = 0 \quad (1)$$

$$\rho \frac{dV}{dt} + \frac{dP}{dx} = 0 \quad (2)$$

where:

S is the arterial lumen area

V is the blood velocity

P is the blood pressure x is the distance along the axis of the vessel t is the time $\rho$ is the volumic density of blood ($10^3$ kg/m$^3$), the relation (1) expressing the conservation of the mass, i.e. of the blood volume, whereas the relation (2) is the hydraulic version of the fundamental dynamics equation.

The elasticity characteristic of the artery can be expressed by the compliance C which is defined by:

$$C = \frac{dS}{dP} \quad (3)$$

which corresponds to the ability of the artery to change its size when the pressure varies. It is shown that the propagation velocity c is directly related to the compliance as follows:

$$C = \frac{S}{\rho c^2} \quad (4)$$

as described in: McDonald's Blood Flow in Arteries, third edition, pp. 85: Wave propagation in elastic tube, by Wilmer W. Nichols and Michael F. O'Rourke, Edward Arnold editor. The relation (4) shows that an accumulated rigidity accelerates the propagation, at the same time reducing the amplitude of the arterial dilatation.

Combination of the relations (3), (4) and (1) results in a new relation:

$$(\rho c^2) \frac{dV}{dx} + \frac{dP}{dt} = 0 \quad (5)$$

By elimination of the parameter P between the equations (5) and (2) and considering that locally the elasticity and hence the propagation velocity c is rendered variable because of plaque or a stenosis, finally there is obtained:

$$\frac{d_2 V}{dt^2} - 2c \left( \frac{dc}{dx} \right) \left( \frac{dV}{dx} \right) - c^2 X \frac{d_2 V}{dx^2} = 0 \quad (6)$$

which is the well-known differential equation of an exponential horn (in the acoustic field). Naturally, herein the perturbation is considered as a constant within the stenosis so that, in a first approximation: $dc/dx = C^{te}$. When the equation (6) is solved, a cut-off pulsation $\omega_c$ is obtained which is expressed by:

$$\omega_c = \left| \frac{dc}{dx} \right| \quad (7)$$

Thus, two types of solution appear:

stationary waves damped for $\omega < \omega_c$:

$$V = e(-mx).[Ae(a(\omega)x) + be(-a(\omega)x)].e(j(\omega)t)$$

where:

$$m = \left| \frac{w_c}{c} \right|, a(\omega) = m\sqrt{\left(1 - \left(\frac{\omega}{\omega_c}\right)^2\right)}$$

progressive waves damped for $\omega > \omega_c$:

$$V = e(-mx).[A.e(j\omega(t-x/c(\omega))) + B.e(j\omega(t+x/c(\omega)))]$$

where:
$m = |\omega_c/c|$, $c(\omega) = c[1-(\omega_c/\omega)^2]^{-\frac{1}{2}}$.

From this analysis it can be extrapolated that as soon as the perturbation of the elasticity is enough to create a cut-off pulsation $\omega_c$ of the same order as the cardiac pulsation, the latter is no longer propagated through the perturbed zone. Moreover, when the pulsation exceeds the limit $\omega_c$, the propagation velocity depends on the value of the pulsation which corresponds to a dispersive propagation. The damping of stationary waves is also dependent on their pulsation: the damping increases as a function of the frequency. The propagation velocity curves and the corresponding damping curves can be plotted as a function of the frequency.

Simple digital applications can help to evaluate the effects caused by the constriction. For example, first of all an axial propagation velocity variation:

$$m = \omega_c/c = (dc/dx)/c = 1\% \text{ per mm}$$

is assumed, so a slight perturbation. For a typical propagation velocity (carotid artery) of c=6 m/s there is found:

$$\omega_c = 2\pi fc = 60 \text{ rd/s, so fc}=10 \text{ Hz.}$$

This signifies that in this case all frequencies below 10 Hz are trapped in the stenosis. The wave associated with the frequency fc=10 Hz is attenuated by $m = 10^{-2}$/mm. A plaque of a length of 1 cm produces an attenuation amounting to $e^{-mx} = 0.90$.

In the case of a severe perturbation such as m=50%/mm and a higher propagation velocity, c=10 m/s (old arteries which are rigid and subject to plaque), fc=5 kHz. It can be considered that in this case there is no longer propagation through the plaque and that all significant frequencies (so in practice the first 15 harmonics) are damped. The attenuation coefficient takes the form:

$$m - a(\omega) = m \ \omega/2 \ \omega_c,$$

revealing a strong deformation of the waveform across the stenosis.

Embodiments of the invention enable validation of the theoretical results indicated above.

A preferred version of the method of detecting and characterizing arterial stenoses is characterized in that said rephased dilatation curves, at the area of the stenosis and its immediate vicinity, are decomposed into their most-significant first harmonics of the cardiac cycle in order to determine a cut-off frequency of value fc with respect to which the stenosis behaves as a high-pass filter for the blood pressure wave along the artery.

Similarly, a preferred version of the apparatus for the characterization of an arterial stenosis is characterized in that said workstation comprises means for analyzing said arterial dilatation curves and for deducing a cut-off frequency fc therefrom which translates the high-pass filter behaviour of said stenosis relative to the blood pressure wave.

BRIEF DESCRIPTION OF THE DRAWING

The following description, given by way of example with reference to the accompanying drawings, will offer a better understanding as to how the invention can be carried out.

FIGS. 4 and 5 show dilatation curves of a segment of an artery which can be obtained in accordance with the invention.

DETAILED DESCRIPTION OF THE PREFERRED EMBODIMENTS

Figure 1:
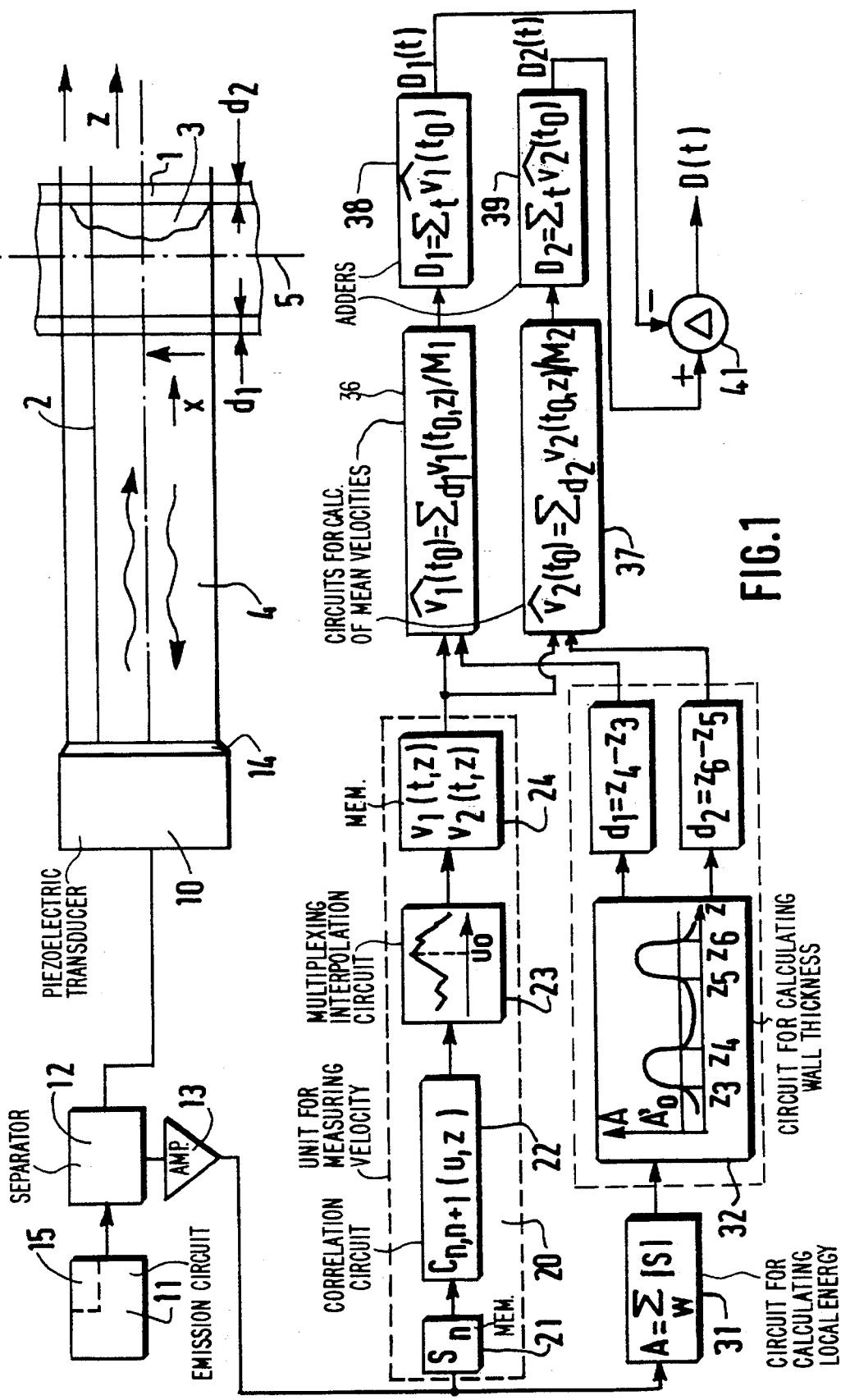
FIG. 1 shows the state of the art for an ultrasonic echograph of the type for signal processing in the time domain, comprising a processing chain for the measurement of the dilatation of an artery.

The diagram of FIG. 1 shows a device for the point-wise measurement of the dilatation of an artery under the influence of the blood pressure. The device comprises a piezo-electric transducer 10 which may be, for example a multi-element array. An emission circuit 11 is connected to the transducer 10 and provides the formation of an ultrasonic scanning beam.

The emission circuit 11 comprises, in a conventional manner, a sequencer which is composed of an oscillator and a frequency divider which controls, at the selected recurrent frequency F, a generator whose electric excitation signals are applied to the transducer 10 which converts these signals into periodic trains of ultrasonic pulse signals. A separator 12 for the emission circuit 11 and the measuring circuit 20 is inserted between the transducer 10 and said circuits 11, 20 and prevents overloading of the measuring circuits by the transmission signals.

The unit 20 for measuring the velocity v(t,z), shown in FIG. 1, receives, after amplification by an amplifier 13, a signal $S_n(t,z)$ from the separator 12, which signal is first stored in a memory 21, after which it is processed in conformity with the so-called correlation method described in the cited European Patent Application No. 0 225 667 which utilizes the fact that the ultrasonic signals returned by a moving target are related by the following equation:

$$S_{n+1}(t) = S_n(t-\tau)$$

which signifies that the signal n+1 is the replica of the preceding signal n, except for a time shift $\tau$. The latter represents the supplementary time necessary for the ultrasonic wave to travel the path from the transducer to the target and back to the transducer again from one excitation to another at the same area, for example the line 2 in FIG. 1. In other words:

$$\tau = 2vT/C_{us}$$

in which v is the velocity of the target and $C_{us}$ is the velocity of sound. It appears that measurement of $\tau$ enables measurement of the velocity v searched.

The correlation function between $S_n(t)$ and $(S_{n+1}(t)$, defined by:

$$C_{n,n+1}(to,u) = \int_{to}^{to+W} S_{n+1}(t+u)S_n(t)dt$$

verifies that $$C_{n,n+1}(to,u) = C_{n,n}(to,u-\tau).$$

The time to is linked to the scanning depth z as to $=2 z/C_{us}$, and W is the width of the integration window.

The function $C_{nn}(to,u)$ is an autocorrelation function and is therefore, maximum for u=0. Thus, a measurement of the time shift $\tau$, and hence of the velocity v, can be performed by searching the parameter u for which the function $C_{n,n+1}(to,u)$ is maximum. To this end, the correlation function is sampled, with a sampling step $\Delta T$, between $u_{min}=-I\Delta t$ and $u_{max}=I\Delta t$ in steps of 1 in order to obtain 2I+1 correlation function values. The maximum value of these 2I+1 values corresponding to u=uo, enables measurement of $\tau$ by utilizing the equality $\tau$=uo. The calculation of the correlation functions is performed by the correlation circuit 22 shown in FIG. 1.

In order to remove the errors which are inherent of sampling in the determination of the maximum of the correlation function, use can be made of a multiplexing-interpolation circuit 23 which supplies, on the basis of the correlation function values, a more exact estimate of the velocity and the value of the corresponding correlation peak. European Patent Application No. 0 225 667 provides an example of this type of echographic signal processing in which the correlation between signals is a so-called 1-bit correlation in a sense that the previously used signals $S_{n+1}$ and $S_n$ are reduced to the sign of the ultrasonic signal. It is known that in this case the correlation function peak is shaped as an isosceles triangle. Knowledge of this shape enables complete reconstruction of the correlation peak by linear-interpolation, starting from the highest point and its two neighbours, and hence accurate determination of the position of uo.

As opposed to conventional Doppler velocimeters, the flow velocity v(t,z) thus determined offers the advantage that it is insensitive to the dispersion of the frequency of the ultrasonic wave used, thus enabling much more complete use of the results.

The values found for the velocity V(t,z) are stored in a memory 24 for later processing.

For the exact calculation of the dilatation D(t) of the artery 1 along the excitation line 2, first of all the thickness of the diametrically opposite walls $d_1(t)$ and $d_2(t)$ is measured. This measurement utilizes, connected to the output of the amplifier 13, a circuit 31 for calculating the local energy:

$$A(t,z) = \sum_w |S(t,z)|$$

and a circuit 32 for calculating wall thicknesses $d_1(t)=z_4(t)-z_3(t)$ and $d_2(t)=z_6(t)-z_5(t)$ which is formed by a threshold detector for an adjustable value $A_o$. In order to avoid any ambiguity as regards the location of the walls, an image of the vessel 1 being studied can be displayed on a screen (not shown) in the mode which is referred to as the M mode for the development in time of the velocity profile of the vessel walls, and the user can localize a point within each wall on the screen, by means of an optical pen (mouse); starting from this point, the summing operations (integrations) can be performed in the direction of the terminals $z_3$ and $z_4$ and $z_5$ and $z_6$, respectively. The coding of the velocity in the mode M is that used in CFM (Colour Flow Mapping) systems; for example, red encodes a direction of motion, blue encodes the reverse direction, and the intensity of the velocity is encoded by the intensity of the colour.

The thicknesses $d_1(t)$ and $d_2(t)$ of the walls being known at any instant $t_0$, the mean velocities $\hat{v}_1(t_o)$ and $\hat{v}_2(t_o)$ of the walls can be calculated by means of the circuits 36 and 37, each of which is formed by an adder and a divider which supply:

$$\hat{v}_1(t_o) = \Sigma_{d1} v_1(t_o,Z)/M_1$$

$$\hat{v}_2(t_o) = \Sigma_{d2} v_2(t_o,Z)/M_2$$

$M_1$ and $M_2$ being the number of measuring samples on the segment $[z_3-z_4]$ and $[z_5-z_6]$, respectively.

A second integration (summing of samples) in time of the mean velocity enables the displacement function of each wall to be accurately obtained; this is realised by the adders 38 and 39:

$$D_1(t) = \sum_{t_0=0}^{t_0=t} \hat{v}_1(t_0)$$

$$D_2(t) = \sum_{t_0=0}^{t_0=t} \hat{v}_2(t_0)$$

It will be noted that the velocities of the walls, perpendicular to those of the blood flow, are very low, i.e. of the order of magnitude of 0.5 cm/s. On the other hand, only the motions of the walls in opposite directions are to be extracted, i.e. the motions which are symmetrical relative to the centre of the vessel. Therefore, it is necessary to eliminate the motions in the same direction, i.e. the asymmetrical motions due to either a lack of equilibrium of the pressure forces to both sides of the vessel, or to the slight movement of the transducer. The mean symmetrical displacement is obtained by way of the subtraction $D(t)=D_2(t)-D_1(t)$ in a subtractor 41.

The invention proposes to realise, at the level of an image (of a frame), what has been described above with reference to FIG. 1 for an excitation line extending perpendicularly to the walls of an artery, notably for an arterial segment such as 1 with a plaque 3 which locally forms a constriction of the lumen area for the passage of the blood (in the direction $\vec{x}$).

It concerns the use of the movement of the arterial wall so as to visualize and evaluate the perturbations of the propagation of waves as caused by the artery. It thus becomes possible to image the arterial dilatation in a non-invasive manner, which dilatation is linked to the pressure as a result of the compliance. However, this implies a scanning process which must be compatible with the time constraints implied by the ultrasonic wave propagation phenomenon. The scanning sequence is then as follows: the transducer array 14 (FIG. 1) being arranged parallel to the artery 1, an excitation plane 4 extending through the axis 5 of the artery is scanned and recorded at a high frame rate of the order of a hundred Hz; this is possible by means of the echograph which is shown at the top in FIG. 1, which utilizes a frame comprising a reduced number of lines L, being of the order of one hundred (for example, 128 excitation lines), and which executes only a single excitation per image line as realised by the first means 15 in the transmission circuit 11 (FIG. 1) as is known to those skilled in the art. For a customary line frequency of 15 kHz, this results in a frame frequency of the order of 10 ms, so a number of images MI of the order of 100 for the duration of one cardiac cycle $T_c$.

Figure 2:
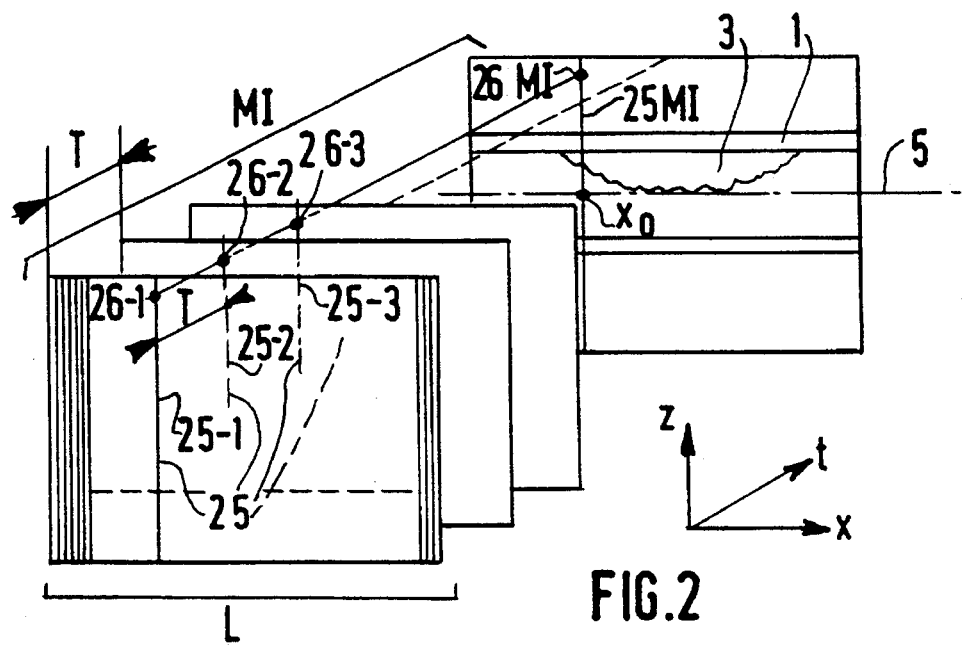
FIG. 2 is a diagrammatic representation of the scanning sequence performed by the echograph so as to carry out the invention.

A correlation method which resembles that described above with reference to the measuring unit 20 is carried out between the recurrent lines of the successive images as shown in FIG. 2. Therein, the line 25 which is situated to the side $x_o$ on the axis $\vec{x}$ and which is chosen as an example from among the L lines of the frame, is equivalent to the line 2 of FIG. 1 with a period between successive excitations which is longer, i.e. equal to the duration of the frame T. The correlations are then performed between the lines 25-1 and 25-2, and then between 25-2 and 25-3, and so on until all MI images of the image sequence have been dealt with; this operation is performed for each of the L image lines.

Figure 3:
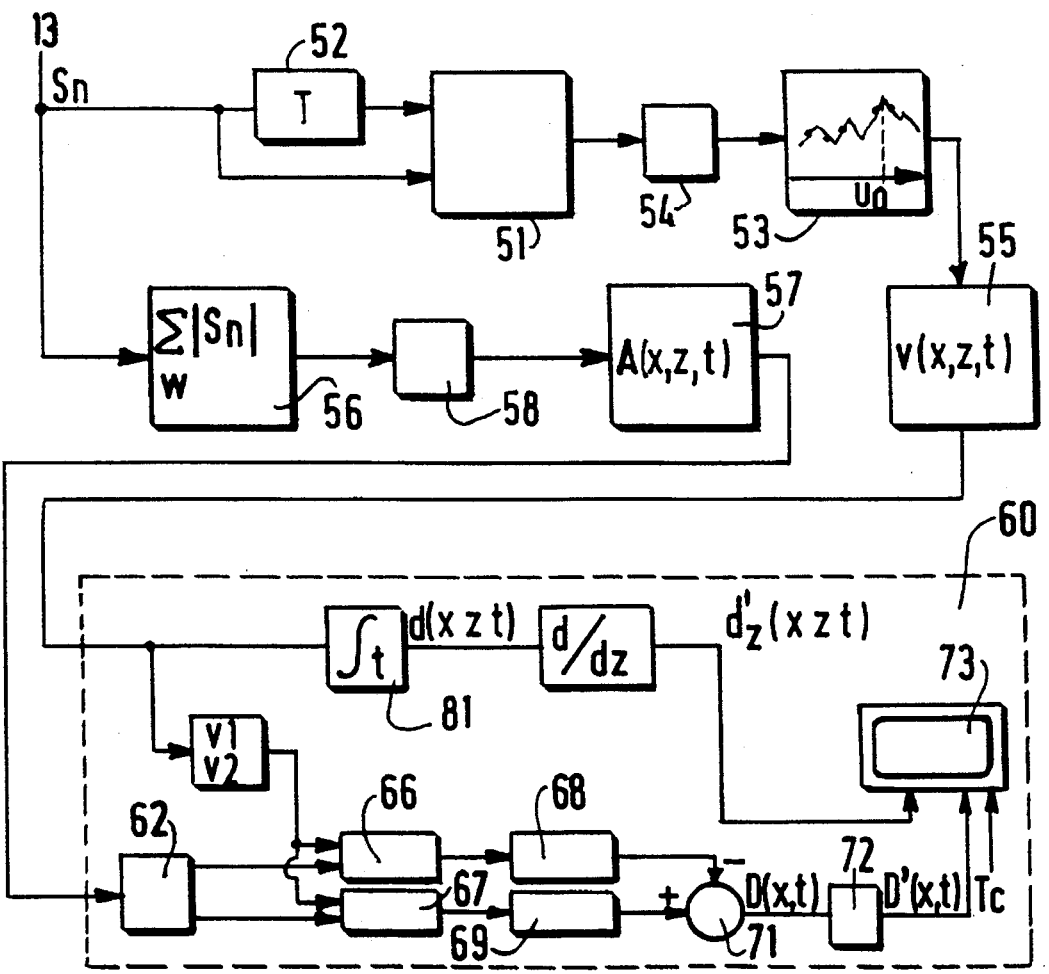
FIG. 3 is a circuit diagram of the apparatus in accordance with the invention.

In order to carry out the invention in practice, an echograph is used for the acquisition of data and a workstation for the processing of these data as shown in FIG. 3.

The scanning described in the foregoing paragraphs results in the current signal $S_n$ from the amplifier 13 in the form of digital samples of a frequency fe of the order of 20 MHz, which is applied to correlation means 51 (preferably a 1-bit correlator) directly and via a delay line 52 in parallel which delays the signal $S_n$ by a frame period T. The correlated signal on the output of the correlator 51 itself is applied to an interpolation device 53 either directly or, as shown in FIG. 3, via signal smoothing means 54 to be described hereinafter. The circuit 53 supplies a memory 55 for a sequence of images in $\vec{x}$ and $\vec{z}$ with radial velocity values v(x,z,t) of the arterial segment 1 analyzed for at least the duration $T_c$ of a cardiac cycle.

The current signal $S_n$ is also applied, in a second processing channel, to a circuit 56 for calculating the amplitude A which implements, for example the function:

$$A = \Sigma_w |S_n|$$

where W is the temporal width of the correlation window, and the signal A(x,z,t) is also applied to a second memory 57 either directly or via signal smoothing means 58 which are analogous to the means 54. For the amplitudes of the echo signals of the image points the memory 57 is the pendant of the memory 55 for the displacement velocities measured for these same points. The first and the second memory can in practice be formed by two different zones of a single, larger memory. The signal smoothing means 54 or 58 serve to realise a sliding average of the values measured for the homologous points of each line (such as 26-1, 26-2, 26-3, ... FIG. 2) over a predetermined, reduced number of images, for example 4 consecutive images. The function to be realised, left up to those skilled in the art, consists in forming the mean value for the points 26-1, 26-2, 26-3, 26-4, subsequently for the points 26-2, 26-3, 26-4, 26-5, and so on until the end of the sequence of the MI images.

The values stored in the memories 55 and 57 are applied to a workstation 60, for example of the type SUN SPARC 10, manufactured by the American company SUN MICROSYSTEM, in which a microprocessor performs the following operations for each of the L image lines:

in 62 the thresholding of the amplitudes A(x,z,t) according to $\vec{z}$ in order to identify the two arterial walls as described above with reference to the circuit 32 of FIG. 1, in 66 and 67 the spatial averaging according to $\vec{z}$ of the velocity information v(x,z,t) in each wall, in 68 and 69 the temporal integration of the mean velocities in each wall in order to supply, for each image line and at any instant of the cardiac cycle, an exact value of the arterial dilatation D(x,t) at the output of a mixer 71.

It is to be noted that the sequence of images of the dilatation to be displayed consists of a succession of instantaneous images formed during the cardiac cycle. The scanning frame employed in the direction $\vec{x}$ in accordance with the invention is of the order of a few meters per second, so of the same order of magnitude as the propagation velocity of the pressure wave along the artery. Therefore, in order to prevent serious falsification of the visualization of the movement of the vessel it is absolutely necessary to rephase the values D(x,t) obtained for each value of x; this is easy to achieve considering that the time shifts between lines are well known because of the constant line frequency (for example, 15 kHz). To this end, a circuit 72 is provided to supply the rephased signals D'(x,t); for example, at the frequency level rephasing of the harmonics can be performed by decomposition of the signal D(x,t) into harmonics, the signal being reconstructed by recomposition on the basis of the most-significant rephased harmonics, for example the first 15 harmonics.

In addition to the described phase restoration, it is advantageous to adjust the dilatation values D(x,t) to be displayed on the screen of a monitor 73 between the beginning and the end of the cardiac cycle $T_c$. Actually, the dilatation is assumed to be zero at the start and at the end of the cardiac cycle. To this end, the completion of the cycle must be known, either by way of an electrocardiogram recorded at the same time as the artery measurement or on the basis of the dilatations of the artery itself, D'(x,t) (in a manner not shown but known to those skilled in the art).

The values of the dilatation curves obtained are positive in the case of a dilatation and negative in the case of a contraction. The curves of FIG. 4 are thus given for a segment of a carotid artery having a length of 2.5 cm and containing a small plaque such as 3 in the FIGS. 1 and 2. The representation used is that which is customarily used for industrial drawing, with a front view according to the plane $\vec{x}, \vec{t}$, a view from the right according to the plane $\vec{z}, \vec{t}$, and a view from below according to the plane $\vec{x}, \vec{z}$. In the view from below the central points constitute the bary centres of given dilatation profiles z(t).

Figure 5A:
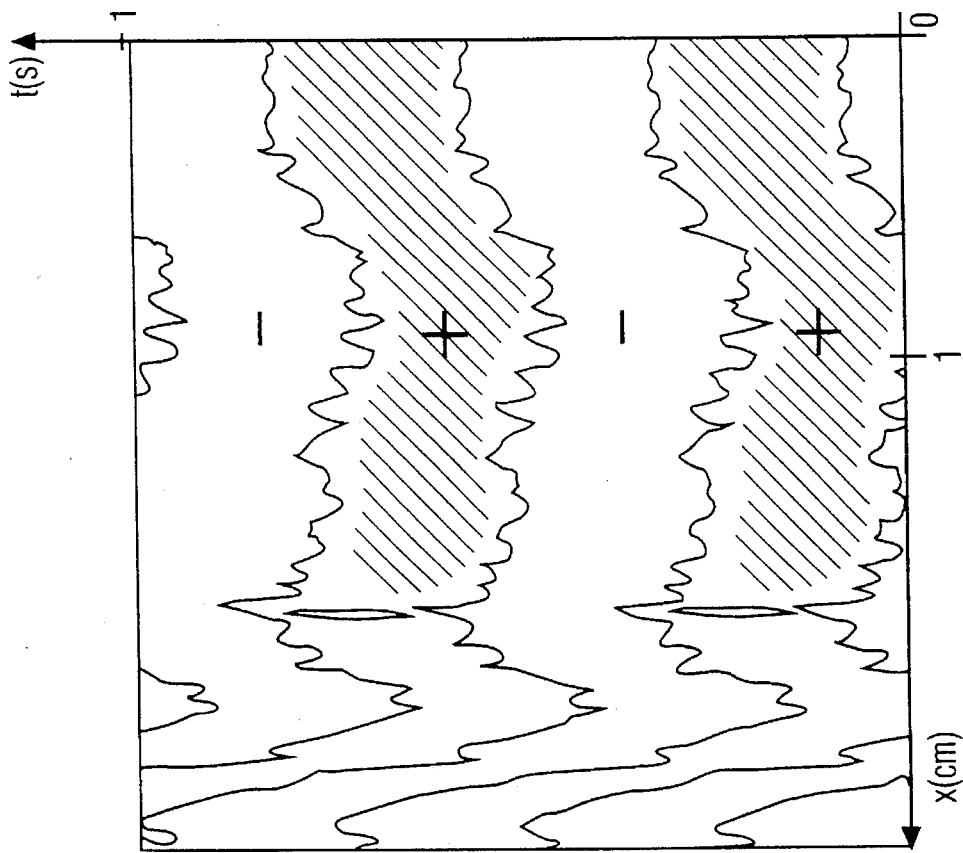
Figure 5B:
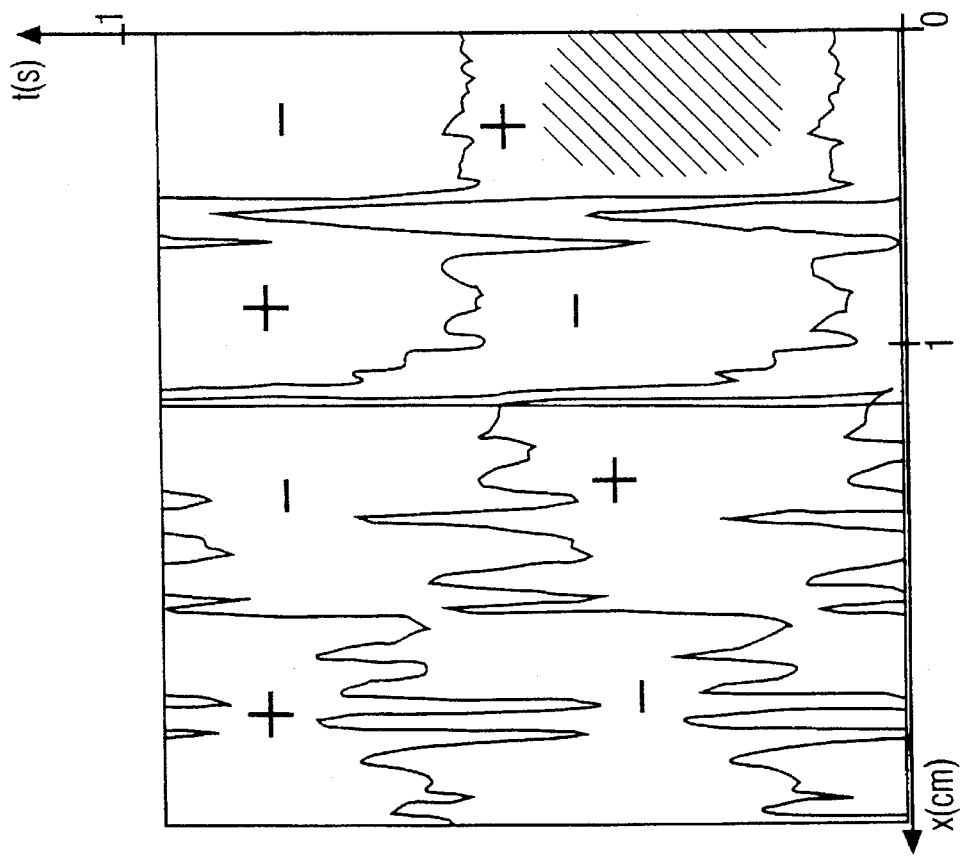

In the example of FIG. 4, the disturbing plaque is considered to be non-pathological by the medical staff. In the plane $\vec{z}, \vec{t}$ the dilatation curves are plotted as a function of time, all curves which correspond to the scanning direction being superposed. In the plane $\vec{x}, \vec{z}$ the excursions of the same dilatation curves occur (between maximum and minimum for each curve) as a function of the transverse scanning position (in $\vec{x}$). The spectacular results offered by these curves reveal a striking behaviour which is not described in the medical files, probably because thus far it has not been possible to demonstrate it: actually, the artery starts to contract, instead of dilate, just downstream from the plaque, denoted by the reference PL. The contraction is of the order of 150 μm whereas the upstream dilatation is approximately 300 μm. A more detailed analysis, compatible with the mathematical analysis discussed above, consists of a decomposition into harmonics. This is represented in FIG. 5 which shows, according to the same conventions as for the view according to the plane $\vec{x}, \vec{t}$ of FIG. 4 (total displacement), the first or fundamental harmonic which is not transmitted because of the plaque (so: $fc > 1/T_c$), and the second harmonic which is transmitted, as well as the subsequent harmonics which are not represented (so: $fc < 2/T_c$). The solid line in the figures in the plane $\vec{x}, \vec{t}$ (FIGS. 4 and 5) marks the points of dilatation zero, constituting a boundary between the dilatation zones (shaded parts indicated by +) and the contraction zones (clear parts indicated by −). Considering the various disturbances in the propagation of these frequencies, it appears that the harmonic 1, corresponding to the cardiac frequency, does not propagate across the plaque: an inversion of sign occurs along the axis x, which is characteristic of stationary waves. The high frequencies succeed in traversing the plaque, even if the amplitudes of the displacements are somewhat attenuated. In this case the cut-off frequency, therefore, is between the first and the second harmonic, more precisely between 1 and 2 Hz. The local disturbance can then be evaluated only as $$\frac{dc}{dx} = 10 s^{-1} = 10^{-2} \left( \frac{m/s}{mm} \right)$$

which appears to be negligible and in conformity with the angiologic diagnosis.

It is also interesting and revealing to calculate, on the basis of the velocity data stored in the memory 55, the displacements of all points tested, followed by a deduction therefrom of the compression images of the biological media traversed.

For this version of the invention the apparatus shown in FIG. 3 comprises a supplementary processing chain in the workstation 60 connected to the output of the memory 55:

first of all, the velocities v(x,z,t) are integrated in respect of time in 81, resulting in the shifts d(x,z,t) of the points of the tissues traversed, subsequently, calculations of the gradient in z of these shifts result in compression data for these tissues, so $d'_z(x,z,t)$, enabling compression images to be obtained on the screen of the monitor 73.

On the monitor of the workstation there can be formed a cinematographic representation of the deformation phenomenon, preferably slowed down at a ratio of the order of 5 with respect to the acquisition time.

This enables a hard fibrous plaque to be distinguished from notably a soft atheroma in a constricted zone of the artery.

I claim:

1. A method of characterizing a segment of an artery by ultrasonic echography, using an array of ultrasonic transducers which produce a sectional plane or frame which is formed by L successive parallel excitation lines in a direction $\vec{z}$ which extends perpendicularly to the axis $\vec{x}$ of the artery, which array is associated with a transmission circuit and a receiving circuit, said echography method including signal processing in the time domain with correlation of the echographic signals relating to said lines and interpolation of the correlated signals in order to determine radial velocities v for points of said sectional plane which are limited to the traversing of the walls of the artery and its immediate vicinity, comprising the steps of:

scanning said frame with a period T of a few ms at a rate of one excitation per line;

performing said correlation and interpolation between collinear excitation lines shifted by the period T in order to obtain, at least for the duration of one cardiac cycle, in a first memory a first sequence of images in $\vec{x}$ and $\vec{z}$ of velocity values v(x,z,t), and in a second memory a second sequence of images in $\vec{x}$ and $\vec{z}$ of amplitude values A(x,z,t); and subsequently using said velocity and amplitude values in a workstation in order to deduce therefrom, by temporal integration of the velocity values, the arterial dilatation curve along each of said L frame lines during at least the period Tc of a cardiac cycle.

2. A method of detecting and characterizing a segment of an artery as claimed in claim 1, characterized in that the following operations are performed by the workstation:

a) the thresholding of the amplitudes in order to identify the two diametrically opposite arterial walls, b) the spatial averaging according to $\vec{z}$ of the velocities in each wall, c) the temporal integration of the two velocities thus averaged, with correction of the movements of the assembly, in order to deduce therefrom the dilatation values D(x,t) of the walls, and the arterial dilatation curves along each of the L frame lines, said curves being associated with the period Tc of the cardiac cycle, d) the rephrasing of said dilatation curves as necessitated by the time shifts imposed on the L lines of each frame.

3. A method as claimed in claim 1, characterized in that it also comprises a supplementary step for calculating the sliding average of the signal between the correlation and 1-bit interpolation phases as well as a supplementary step for calculating the sliding average of the signal which is representative of the amplitudes A(x,z,t) before writing into said second memory.

4. A method as claimed in claim 1 for detecting and characterizing arterial stenoses, characterized in that said rephased dilatation curves, at the area of the stenosis and its immediate vicinity, are decomposed into their most-significant first harmonics of the cardiac cycle in order to determine a cut-off frequency of value fc with respect to which the stenosis behaves as a high-pass filter for the blood pressure wave along the artery.

5. A method for detecting and characterizing stenoses as claimed in claim 1, characterized in that it comprises a supplementary step for calculating the gradient in the direction $\vec{z}$ of the elongation values d(x,z,t) obtained by temporal integration of the velocities v(x,z,t) contained in said first memory and enabling the formation, during the last step, of compression images for the walls of the arterial segment analyzed and the adjoining tissues.

6. An apparatus for detecting and characterizing an arterial segment, comprising an ultrasonic echograph and a workstation, the echograph consisting of a probe provided with an array of ultrasonic transducers for emitting a frame of L successive lines during a period T in a direction $\vec{z}$ which extends perpendicularly to the axis $\vec{x}$ of the artery, an emission circuit and a receiving circuit for signal processing in the time domain comprising correlation means and interpolation means for the echographic signals, said emission circuit comprising first means for performing a single excitation per frame line, said receiving circuit comprising second means for performing correlation and interpolation between collinear excitation lines shifted by the period T, said echograph also comprising a first memory for a sequence of images in $\vec{x}$ and $\vec{z}$ of velocity values v(x,z,t) and a second memory for a sequence of images in $\vec{x}$ and $\vec{z}$ of amplitude values A(x,z,t) for the duration of at least one cardiac cycle, and said workstation comprising means for utilizing the contents of said first and second memory and for deducing therefrom elongation values as well as dilatation curves for the arterial segment analyzed.

7. An apparatus as claimed in claim 6, characterized in that said receiving circuit also comprises signal smoothing means which are arranged between said correlation means, being 1-bit correlation means, and the interpolation means, and also comprises smoothing means for the amplitude signal which are arranged just upstream from said second memory.

8. An apparatus as claimed in claim 6, characterized in that said workstation comprises:

a) thresholding means for thresholding said amplitudes A(x,z,t) according to $\vec{z}$ in order to identify the two arterial walls, b) averaging means for forming a spatial means value according to $\vec{z}$ of the velocity information v(x,z,t) in each wall, c) integration means for performing the integration in time of the two velocities thus averaged, including correction of the movements of the assembly in order to deduce therefrom the dilatation values D(x,t) of the walls, and the arterial dilatation curves along each of the L frame lines, said curves being associated with the period of the cardiac cycle, d) dephasing means for performing the rephrasing of said dilatation curves as necessitated by the time shifts imposed on the L lines of each frame.

9. An apparatus as claimed in claim 8, conceived for the characterization of an arterial stenosis, characterized in that said workstation comprises means for analyzing said arterial dilatation curves and for deducing a cut-off frequency fc therefrom which translates the high-pass filter behaviour of said stenosis relative to the blood pressure wave.

10. An apparatus as claimed in claim 6, characterized in that said workstation comprises integration means for performing the temporal integration of the velocities v(x,z,t) and for deriving therefrom the elongation values d(x,z,t), and calculation means for calculating the gradient in the direction $\vec{z}$ of said elongation values d(x,z,t) and for deriving therefrom compression images for the walls of the arterial segment analyzed and the adjacent tissues.

11. A method as claimed in claim 2, characterized in that it also comprises a supplementary step for calculating the sliding average of the signal between the correlation and 1-bit interpolation phases as well as a supplementary step for calculating the sliding average of the signal which is representative of the amplitudes A(x,z,t) before writing into said second memory.

12. A method as claimed in claim 2 for detecting and characterizing arterial stenoses, characterized in that said rephased dilatation curves, at the area of the stenosis and its immediate vicinity, are decomposed into their most-significant first harmonics of the cardiac cycle in order to determine a cut-off frequency of value fc with respect to which the stenosis behaves as a high-pass filter for the blood pressure wave along the artery.

13. A method as claimed in claim 11 for detecting and characterizing arterial stenoses, characterized in that said rephased dilatation curves, at the area of the stenosis and its immediate vicinity, are decomposed into their most-significant first harmonics of the cardiac cycle in order to determine a cut-off frequency of value fc with respect to which the stenosis behaves as a high-pass filter for the blood pressure wave along the artery.

14. A method for detecting and characterizing stenoses as claimed in claim 2, characterized in that it comprises a supplementary step for calculating the gradient in the direction $\vec{z}$ of the elongation values d(x,z,t) obtained by temporal integration of the velocities v(x,z,t) contained in said first memory and enabling the formation, during the last step, of compression images for the walls of the arterial segment analyzed and the adjoining tissues.

15. A method for detecting and characterizing stenoses as claimed in claim 13, characterized in that it comprises a supplementary step for calculating the gradient in the direction $\vec{z}$ of the elongation values d(x,z,t) obtained by temporal integration of the velocities v(x,z,t) contained in said first memory and enabling the formation, during the last step, of compression images for the walls of the arterial segment analyzed and the adjoining tissues.

16. An apparatus as claimed in claim 7, characterized in that said workstation comprises:

a) thresholding means for thresholding said amplitudes A(x,z,t) according to $\vec{z}$ in order to identify the two arterial walls, b) averaging means for forming a spatial means value according to $\vec{z}$ of the velocity information v(x,z,t) in each wall, c) integration means for performing the integration in time of the two velocities thus averaged, including correction of the movements of the assembly in order to deduce therefrom the dilatation values D(x,t) of the walls, and the arterial dilatation curves along each of the L frame lines, said curves being associated with the period of the cardiac cycle, d) dephasing means for performing the rephrasing of said dilatation curves as necessitated by the time shifts imposed on the L lines of each frame.

17. An apparatus as claimed in claim 7, conceived for the characterization of an arterial stenosis, characterized in that said workstation comprises means for analyzing said arterial dilatation curves and for deducing a cut-off frequency fc therefrom which translates the high-pass filter behaviour of said stenosis relative to the blood pressure wave.

18. An apparatus as claimed in claim 7, characterized in that said workstation comprises integration means for performing the temporal integration of the velocities v(x,z,t) and for deriving therefrom the elongation values d(x,z,t), and calculation means for calculating the gradient in the direction $\vec{z}$ of said elongation values d(x,z,t) and for deriving therefrom compression images for the walls of the arterial segment analyzed and the adjacent tissues.

19. An apparatus as claimed in claim 8, characterized in that said workstation comprises integration means for performing the temporal integration of the velocities v(x,z,t) and for deriving therefrom the elongation values d(x,z,t), and calculation means for calculating the gradient in the direction $\vec{z}$ of said elongation values d(x,z,t) and for deriving therefrom compression images for the walls of the arterial segment analyzed and the adjacent tissues.

* * * * *